US009597199B2

(12) United States Patent
Glazer

(10) Patent No.: US 9,597,199 B2
(45) Date of Patent: *Mar. 21, 2017

(54) ORTHOPEDIC IMPLANTS WITH FLEXIBLE SCREWS

(71) Applicant: Paul A. Glazer, Chestnut Hill, MA (US)

(72) Inventor: Paul A. Glazer, Chestnut Hill, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/659,214

(22) Filed: Mar. 16, 2015

(65) Prior Publication Data

US 2015/0265418 A1    Sep. 24, 2015

Related U.S. Application Data

(63) Continuation of application No. 13/355,875, filed on Jan. 23, 2012, now Pat. No. 8,979,930.

(51) Int. Cl.
*A61F 2/44* (2006.01)
*A61F 2/46* (2006.01)
(Continued)

(52) U.S. Cl.
CPC .............. *A61F 2/4465* (2013.01); *A61F 2/30* (2013.01); *A61F 2/30771* (2013.01);
(Continued)

(58) Field of Classification Search
CPC .......... A61B 17/8057; A61B 2017/681; A61B 17/1728; A61B 17/7233; A61B 17/809; A61B 17/8052
(Continued)

(56) References Cited

U.S. PATENT DOCUMENTS 4,961,740 A   10/1990 Ray et al.
5,871,486 A    2/1999 Huebner et al.
(Continued)

FOREIGN PATENT DOCUMENTS

FR       2954692 A1    7/2011
WO   WO-9703611 A1    2/1997
(Continued)

OTHER PUBLICATIONS

VerteBRIDGE, Plating Technology, LDR Spine—verteBridge website, 2011.

*Primary Examiner* — Mary Hoffman
*Assistant Examiner* — Tara R Carter
(74) *Attorney, Agent, or Firm* — Locke Lord LLP; Joshua L. Jones; Alicia J. Carroll

(57) ABSTRACT

An orthopedic implant system includes an implant configured and adapted for orthopedic applications. The implant defines a bore therethrough having a bore entrance defined along a first axis and a bore exit defining a second axis that is angled with respect to the first axis to facilitate implantation of the implant. A flexible screw is mounted in the bore of the implant. The screw includes a head at one end configured to receive a driver tool for turning the screw within the implant, and a screw tip at an opposite end from the head configured for engaging bone. A portion of the screw between the tip and the head is flexible to allow bending of the screw while passing into the bore of the implant along the first axis and out of the bore of the implant along the second axis.

21 Claims, 11 Drawing Sheets

(51) Int. Cl.
*A61F 2/30* (2006.01)
*A61B 17/86* (2006.01)

(52) U.S. Cl.
CPC .............. *A61F 2/442* (2013.01); *A61F 2/447* (2013.01); *A61F 2/4611* (2013.01); *A61B 17/866* (2013.01); *A61B 17/8625* (2013.01); *A61F 2002/3041* (2013.01); *A61F 2002/30092* (2013.01); *A61F 2002/30774* (2013.01); *A61F 2002/30777* (2013.01); *A61F 2002/30779* (2013.01); *A61F 2002/30787* (2013.01); *A61F 2002/30904* (2013.01); *A61F 2002/4475* (2013.01); *A61F 2310/00017* (2013.01); *A61F 2310/00023* (2013.01); *A61F 2310/00029* (2013.01)

(58) Field of Classification Search
USPC ................... 606/246–249, 280–299, 62–68; 623/17.11–17.16
See application file for complete search history.

(56) References Cited

U.S. PATENT DOCUMENTS

| | | | |
|---|---|---|---|
| 6,447,518 | B1 | 9/2002 | Krause et al. |
| 7,887,595 | B1 | 2/2011 | Pimenta |
| 8,523,945 | B1 | 9/2013 | Wensel |
| 2006/0136063 | A1 | 6/2006 | Zeegers |
| 2006/0195099 | A1 | 8/2006 | Bottlang |
| 2007/0179624 | A1 | 8/2007 | Stone et al. |
| 2008/0243136 | A1 | 10/2008 | Prager et al. |
| 2008/0262318 | A1 | 10/2008 | Gorek et al. |
| 2009/0132054 | A1 | 5/2009 | Zeegers |
| 2010/0094361 | A1 | 4/2010 | Meneghini et al. |
| 2011/0144703 | A1 | 6/2011 | Krause et al. |
| 2012/0078373 | A1 | 3/2012 | Gamache et al. |

FOREIGN PATENT DOCUMENTS

| | | |
|---|---|---|
| WO | WO-2008100590 A1 | 8/2008 |
| WO | WO-2008149223 A2 | 12/2008 |
| WO | WO-2010099239 A2 | 9/2010 |

ORTHOPEDIC IMPLANTS WITH FLEXIBLE SCREWS

CROSS-REFERENCE TO RELATED APPLICATIONS

This application is a continuation of U.S. patent application Ser. No. 13/355,875 filed Jan. 23, 2012, which is incorporated by reference herein in its entirety.

BACKGROUND OF THE INVENTION

1. Field of the Invention

The present invention relates to orthopedics, and more particularly to implants and procedures for orthopedic applications.

2. Description of Related Art

A variety of devices and procedures are known in the art for implanting devices in orthopedic applications, such as intervertebral implants, acetabular cups, and glenoid fossa prostheses. As one example, intervertebral spacers are usually made of PEEK, bone, or titanium. They are used to restore disc height and create a rigid anterior spinal column which assists in fusion rates. Intervertebral spacers have been made in a variety of shapes but routinely simulate the vertebral body structure in an effort to rest on the cortical rim which consists of denser bone than the cancellous bone found in the center of the endplates. Spacers resting primarily on cancellous bone would subside because cancellous bone is less dense, and the subsidence would reduce the effect of expansion of intervertebral height and neuroforaminal space thereby leading to nerve impingement. Spacers are often made with ridges on the top and bottom surfaces to resist displacement. Additionally, screws have been used to supplement the fixation and rigidity of the construct.

When utilizing an intervertebral spacer as a lumbar implant, for example, the surgeon typically applies the implant through an abdominal anterior or lateral incision via a retro- or transperitoneal approach. Given the significant distance from the abdominal wall to the anterior spine due to the girth of the patient, which can be even greater for larger patients, application of the interbody spacers and fixation can pose a difficult challenge. The implants are routinely placed into the disc space in a linear fashion using implements at the end of long, straight instruments.

The application of additional fixation with current screw technology often proves extremely difficult given the limited angles which can be obtained for long instruments through a small incision often as far as 8-12 inches from the spine. Many traditional spacers have oblique slots for screws to pass in through the side of the spacers that face the surgeon during implantation, and out the superior or inferior side of the spacer to allow for direct fixation from the spacer to the adjacent vertebra. These oblique slots are usually applied at angles of 30° to 45° relative to the top and bottom surfaces of the spacers. Due to geometrical limitations of typical incisions described above, the oblique slots require the use of screw drivers, drills, and/or awls employing universal joints near their distal ends. These instruments can be dangerous to use because of the requirement for the surgeon to apply a translational force to the head of the instrument to engage the implant obliquely, which can lead to slipping. Slipping with such an instrument can cause damage to the adjacent vascular and visceral structures which are immediately adjacent to the spine and are often retracted at the time of application of the implants.

Such conventional methods and systems have generally been considered satisfactory for their intended purpose. However, there is still a need in the art for methods and devices that allow for improved application of orthopedic implants. There also remains a need in the art for such implants that are easy to make and use. The present invention provides a solution for these problems.

SUMMARY OF THE INVENTION

The subject invention is directed to a new and useful orthopedic implant system. The system includes an implant configured and adapted for implantation in orthopedic applications. The implant defines a bore therethrough having a bore entrance defined along a first axis and a bore exit defining a second axis that is angled with respect to the first axis to facilitate implantation of the implant. A flexible screw is mounted in the bore of the implant. The screw includes a head at one end configured to receive a driver tool for turning the screw within the implant, and a screw tip at an opposite end from the head configured for engaging bone. A portion of the screw between the tip and the head is flexible to allow bending of the screw while passing into the bore of the implant along the first axis and out of the bore of the implant along the second axis.

In certain embodiments, the implant includes a camming surface in the bore for turning the tip of the flexible screw from the first axis to the second axis as the flexible screw is advanced within the bore. The implant can be an intervertebral spacer, an acetabular cup, a glenoid fossa prosthesis, scaphoid prosthesis, or any other suitable type of implant.

In accordance with certain embodiments, the implant is an intervertebral spacer that includes opposed superior and inferior surfaces configured and adapted for engaging the spacer between a superior vertebra and an inferior vertebra, respectively. The first axis and bore entrance can be substantially parallel to the superior and inferior surfaces of the spacer, and the bore exit and second axis can be angled with respect to the first axis at an angle in the range of about 30° to about 45°. The spacer can include a second bore therethrough having a bore entrance defined along a third axis parallel to the first axis and a bore exit defining a fourth axis that is angled with respect to the third axis. The bore exit of the first bore can open on the superior surface of the spacer, and the bore exit of the second bore can open on the inferior surface of the spacer. The spacer can further include a third bore therethrough having a bore entrance defined along a fifth axis parallel to the first axis and a bore exit defining a sixth axis that is angled with respect to the fifth axis, wherein the bore exit of the third bore opens on the inferior surface of the spacer.

The invention also provides a method of implanting an implant for orthopedic applications. The method includes inserting an implant as described above into an orthopedic implant location. The method also includes affixing the implant to a bone by driving a flexible screw in through the bore entrance along the first axis and out through the bore exit along the second axis and into the bone.

Inserting an implant can include inserting the implant into an orthopedic implant location between an inferior vertebra and a superior vertebra. Driving a flexible screw can include driving the flexible screw through the bore entrance along the first axis with the first axis substantially perpendicular to an inferior-superior direction defined by the inferior and superior vertebrae. The implant location can be in a cervical spine, thoracic spine, lumbar spine, glenohumoral joint, hip joint, wrist, or any other suitable location. For example, the implant can be inserted between two vertebrae from an anterior approach, a lateral approach, or a posterior approach.

Affixing the implant to a bone can include compressing the implant and the bone together with a flexible screw that has a first screw pitch at a proximal end of the screw and a second screw pitch at a distal end of the screw for compressing the bone and implant together. Driving the flexible screw can include turning the flexible screw with a driver tool engaged to a proximal end of the screw while camming a distal tip of the screw in the bore of the implant to bend the flexible screw and impart an angle of about 30° to about 45° on the distal tip of the screw with respect to the first axis. It is also contemplated that affixing the implant can include affixing the implant to a second bone by driving a second flexible screw in through an entrance of a second bore in the implant along a third axis parallel with the first axis and out through a respective bore exit along a fourth axis angled relative to the third axis and into a second bone.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF THE PREFERRED EMBODIMENTS

Figures 1, 2:
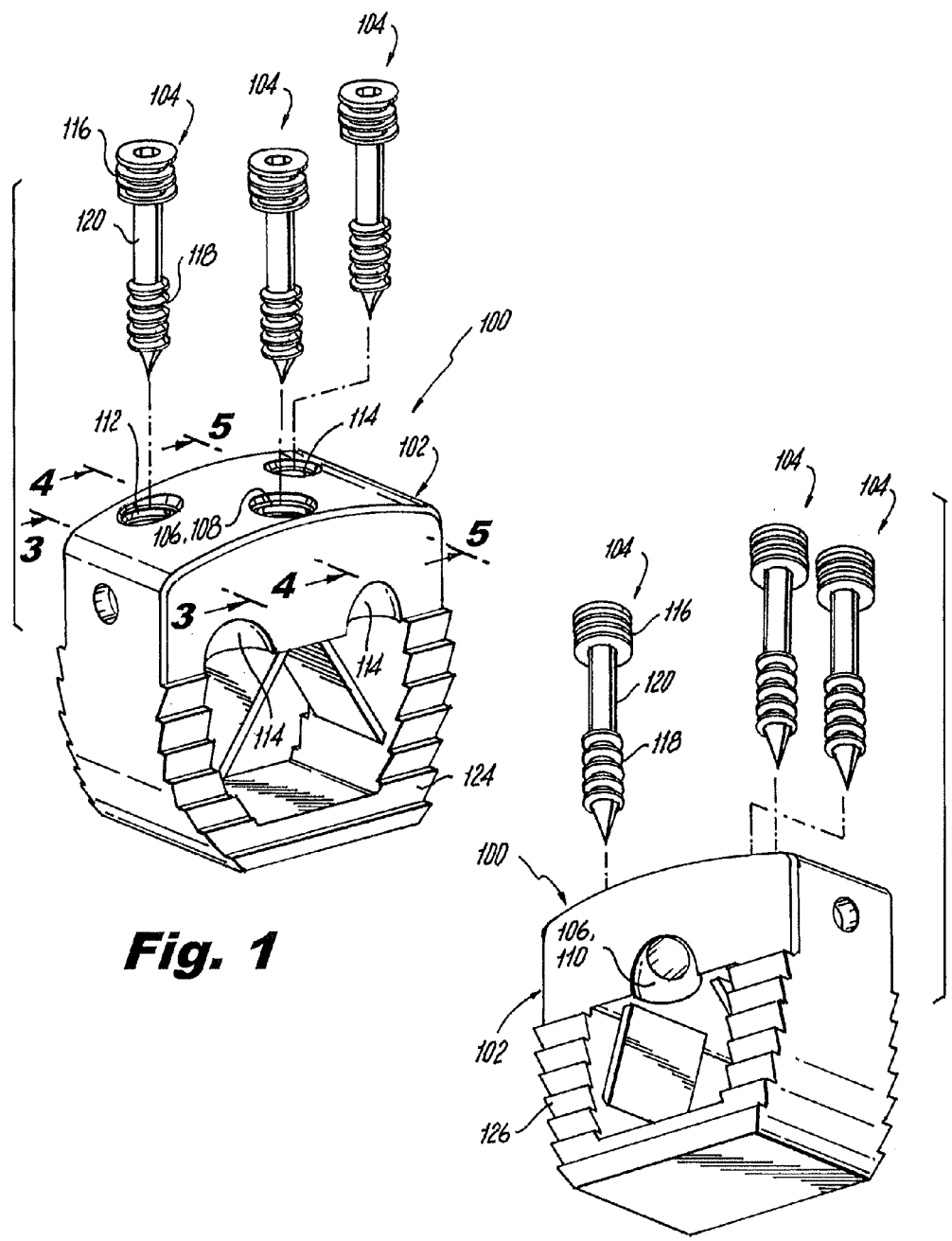
FIG. 1 is an exploded perspective view of an exemplary embodiment of an orthopedic implant system constructed in accordance with the present invention, showing an intervertebral spacer with three flexible Herbert screws.
FIG. 2 is a perspective view of the orthopedic implant system of FIG. 1, showing the opposite side of the spacer from that shown in FIG. 1.

Reference will now be made to the drawings wherein like reference numerals identify similar structural features or aspects of the subject invention. For purposes of explanation and illustration, and not limitation, a partial view of an exemplary embodiment of an orthopedic implant system in accordance with the invention is shown in FIG. 1 and is designated generally by reference character 100. Other embodiments of orthopedic implant systems in accordance with the invention, or aspects thereof, are provided in FIGS. 2-13, as will be described. The system of the invention can be used to facilitate application of orthopedic implants such as intervertebral spacers.

Implant system 100 includes an intervertebral spacer 102 and three flexible Herbert screws 104. Spacer 102 is implant configured and adapted for implantation in between two vertebrae. Spacer 102 includes a medial bore 106 therethrough having a 108 and a bore exit 110, which is shown in FIG. 2. Spacer 102 also includes a first lateral bore 112 and a second lateral bore 114. Each of the first and second lateral bores 112 and 114 has a bore entrance on the same side of spacer 102 as entrance 108 of medial bore 106, but the bore exits for the lateral bores 112 and 114 are on the opposite side of spacer 102 from bore exit 110 of medial bore 106.

Each screw 104 includes a head 116 at one end configured to receive a driver tool for turning the screw, and a screw tip 118 at the opposite end for engaging bone. A shaft 120 forms a portion of each screw between tip 118 and head 116 that is flexible to allow bending of the screw 104 while passing into the respective bore of spacer 102. The flexible shaft 120 can be a tube with interlocking helical cut sections, and can optionally be cannulated so that it can be placed over a guidewire. Further details of flexible screws can be found in U.S. Patent Application Serial No. 2011/0144703 to Krause et al., which is incorporated by reference herein in its entirety. Other exemplary bendable shaft forms include any other suitable interlocking helical cuts, other laser cut designs, flexible materials such as nitinol, shape memory alloys, helical cut tubes, or any other form of bendable shaft suitable for providing both adequate flexibility and developing adequate torque for driving the threads into place.

Figure 3:
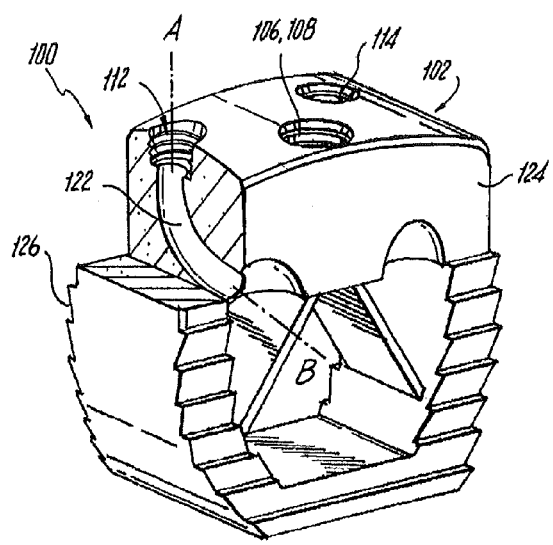
FIG. 3 is a cut away perspective view of the spacer of FIG. 1, showing the cross-section of the first lateral bore through the spacer for receiving and bending one of the screws of FIG. 1.

Referring now to FIG. 3, first lateral bore 112 includes a camming surface 122 for turning the tip 118 of flexible screw 104 as it is driven through spacer 102. Each of the bores defines a first axis at its entry, e.g., axis A in FIG. 3, and a second axis at its exit, e.g. axis B in FIG. 3, that is angled with respect to the first axis, i.e., axis B is angled relative to axis A. As a screw 104 is driven into its respective bore 106, 112, or 114, the shaft 120 of the screw bends to conform to the camming surface 122 of the bore. This turns the tip 118 of the screw from the first axis to the second axis as the flexible screw is advanced within the bore.

Figure 4:
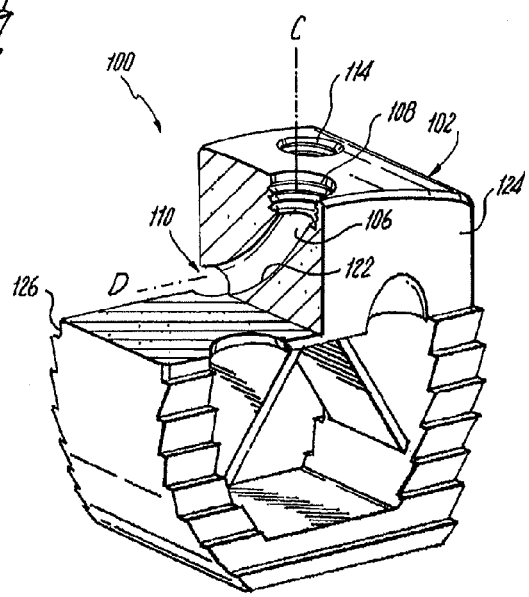
FIG. 4 is a cut away perspective view of the spacer of FIG. 1, showing the cross-section of the medial bore of the spacer.
Figure 5:
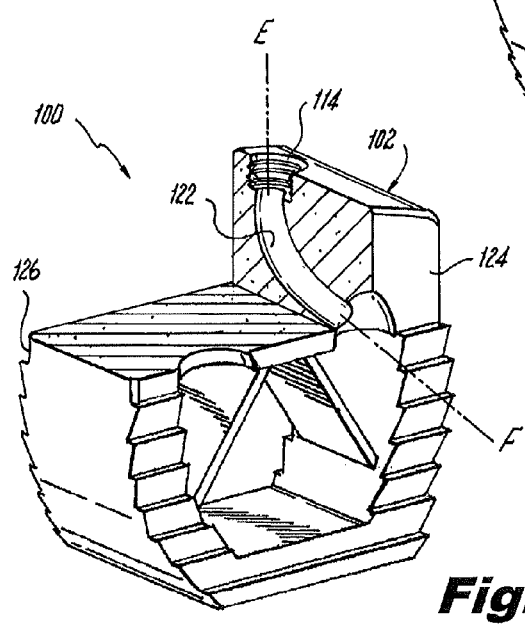
FIG. 5 is a cut away perspective view of the spacer of FIG. 1, showing the cross-section of the second lateral bore through the spacer.

FIGS. 4 and 5 show the cross sections of the respective bores 106 and 114, and respective angled axes C, D, E, and F. All of the exit axes B, D, and F are angled at about 30° relative to their respective entrance axes A, C, and E. This angle can be as much as about 45°, or any other suitable angle for a given application without departing from the spirit and scope of the invention. Moreover, the entrance and exit axes along which the screw is bent need not correspond to the local center of the bore at the entrance and exit, but rather define the entrance and exit path of the screw when positioned in the bore. For example if there is play between the bore and the screw, the screw may not precisely conform to the angles of the bore entrance and exit, but will nonetheless bend when driven through the bore.

Spacer 102 includes opposed inferior and superior surfaces 124 and 126 which are shaped and textured for engaging the spacer between a superior vertebra and an inferior vertebra, respectively. The surfaces 124 and 126 are substantially parallel to each other, and can be angled slightly relative to one another to accommodate the lordotic anatomy of the intervertebral space. The first axis, e.g., axes A, C, and E, and bore entrances, e.g., 108, are substantially parallel to each other and to the inferior and superior surfaces 124 and 126 of spacer 102. If surfaces 124 and 126 are significantly angled relative to one another to accommodate lordotic anatomy, axes A, C, and E can be angled so as to allow the screws 104 to enter the bores 106, 112, and 114 in a direction perpendicular to the local spine. Bore exit 110 of first bore 106 opens on superior surface 126, and the bore exits of the lateral bores 112 and 114 open on inferior surface 124.

Figure 6:
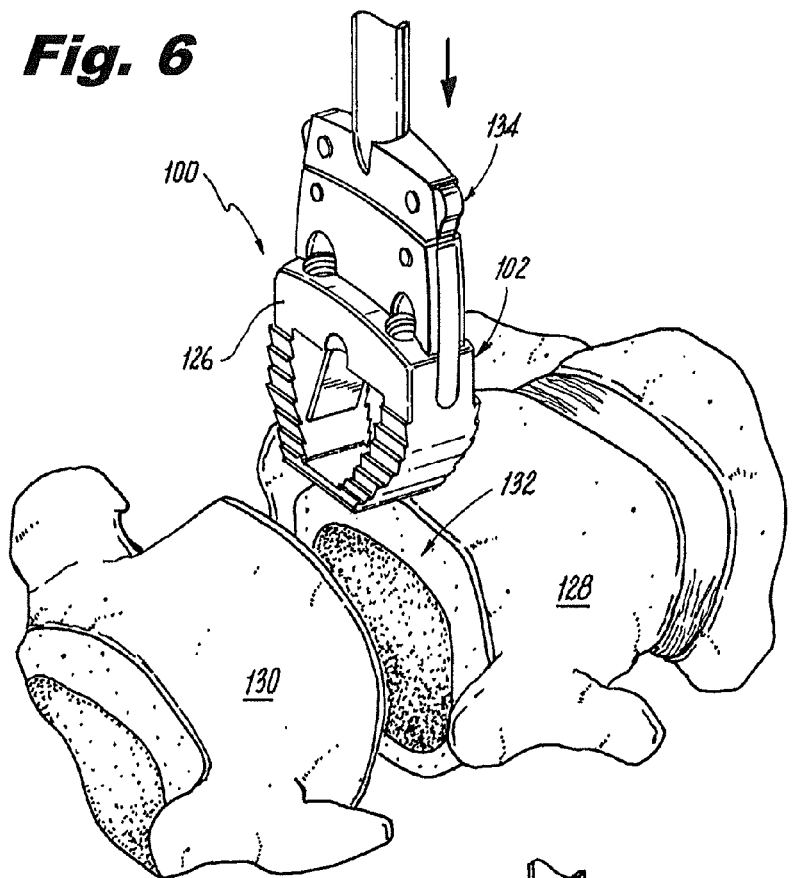
FIG. 6 is a schematic perspective view of the spacer of FIG. 1, showing the spacer being inserted at the end of an insertion instrument into the intervertebral space between two vertebrae.
Figure 7:
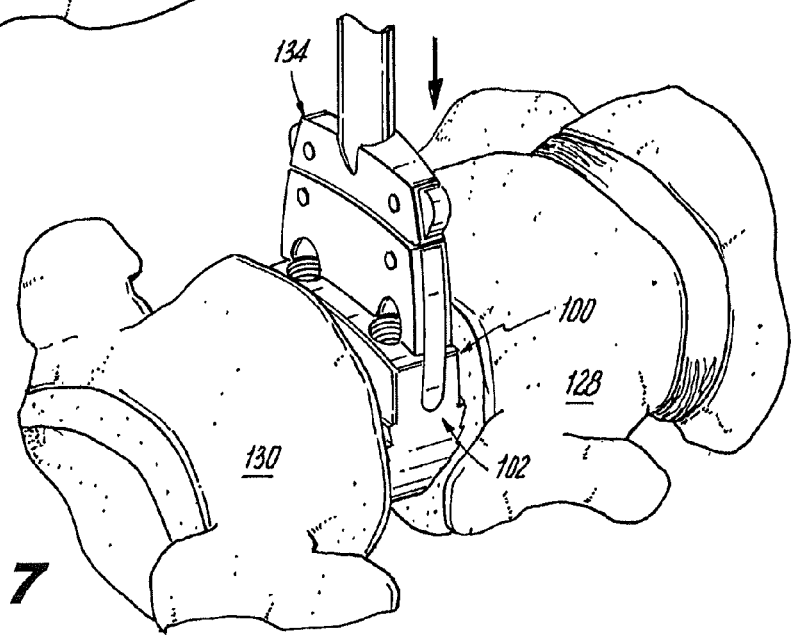
FIG. 7 is a schematic perspective view of the spacer of FIG. 6, showing the spacer positioned in the intervertebral space for implantation.

Referring now to FIG. 6, an inferior vertebra 128 and superior vertebra 130 are shown with the intervertebral disc space 132 prepared for implantation of spacer 102, i.e., the disc has been removed. Implant 102 is inserted into intervertebral space 132 using inserter 134 as indicated by the arrows in FIGS. 6 and 7 until reaching the position shown in FIG. 7, which is the implant location. Once spacer 102 is in a suitable position, it can be released from the grips of inserter 134, which can be withdrawn.

Figures 8, 9:
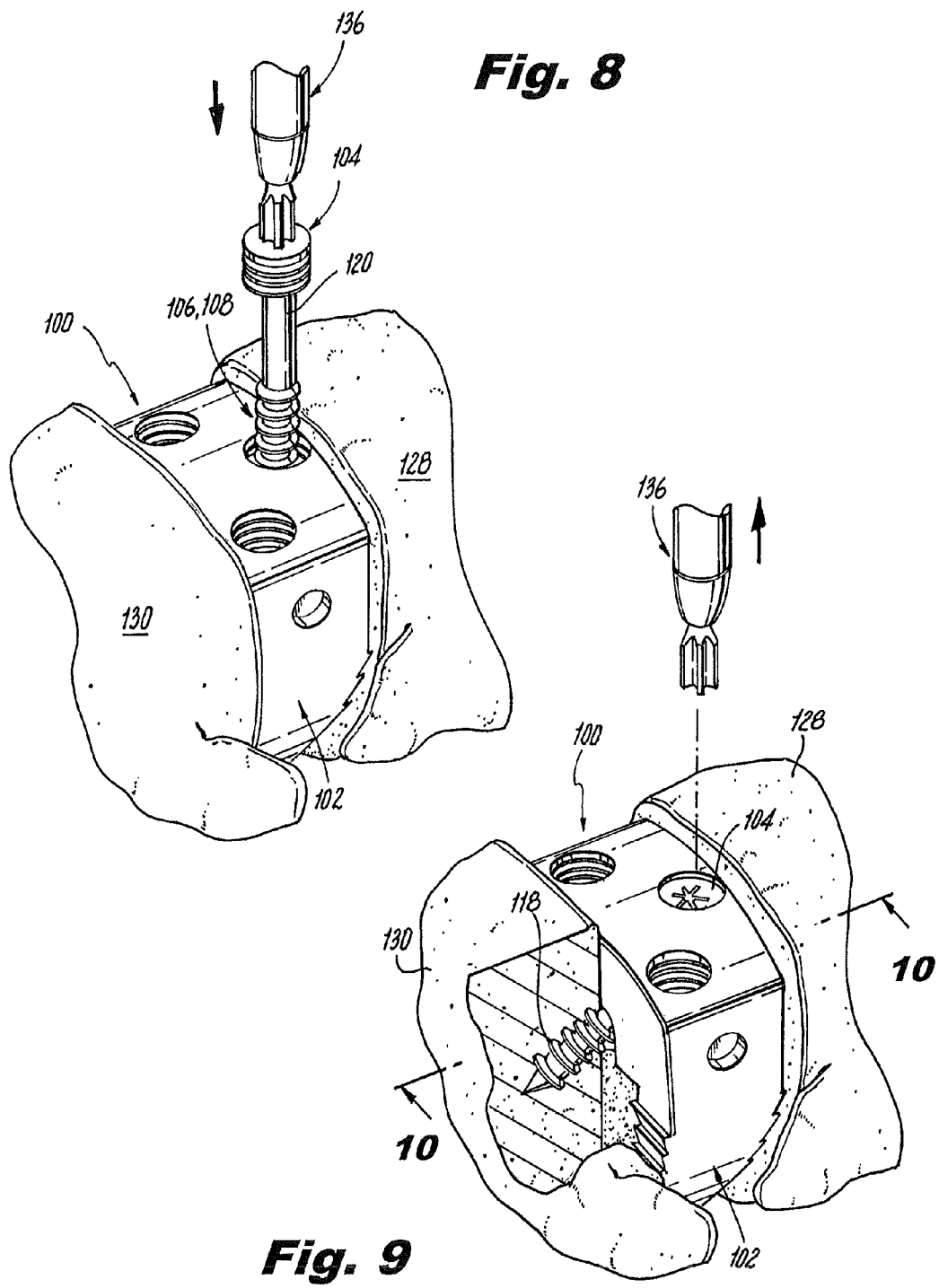
FIG. 8 is a schematic perspective view of the spacer of FIG. 7, showing the medial screw being driven into the medial bore of the spacer.
FIG. 9 is a cut away schematic perspective view of the spacer of FIG. 8, showing the medial screw affixed to the first vertebra.
Figure 10:
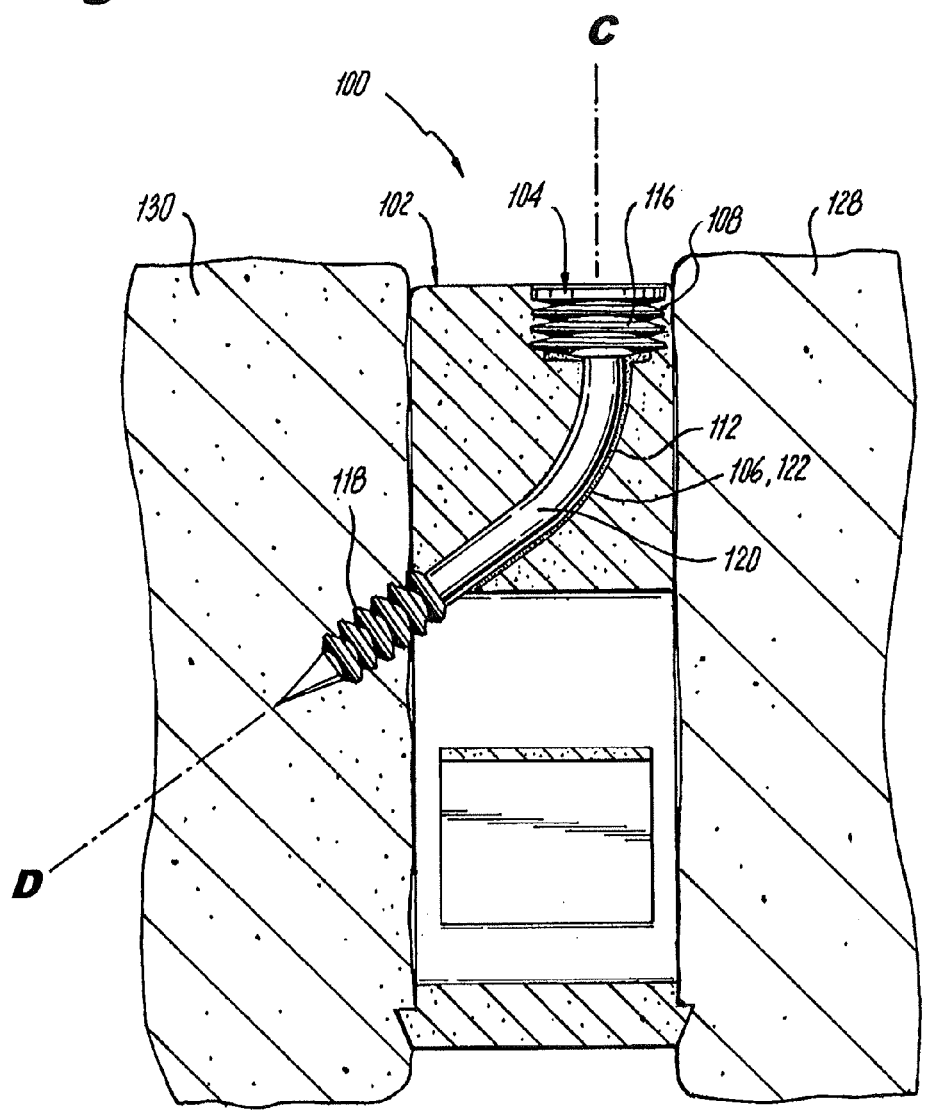
FIG. 10 is a schematic cross-sectional elevation view of the spacer of FIG. 9, showing the medial screw in place joining the spacer and the first vertebra together.
Figure 11:
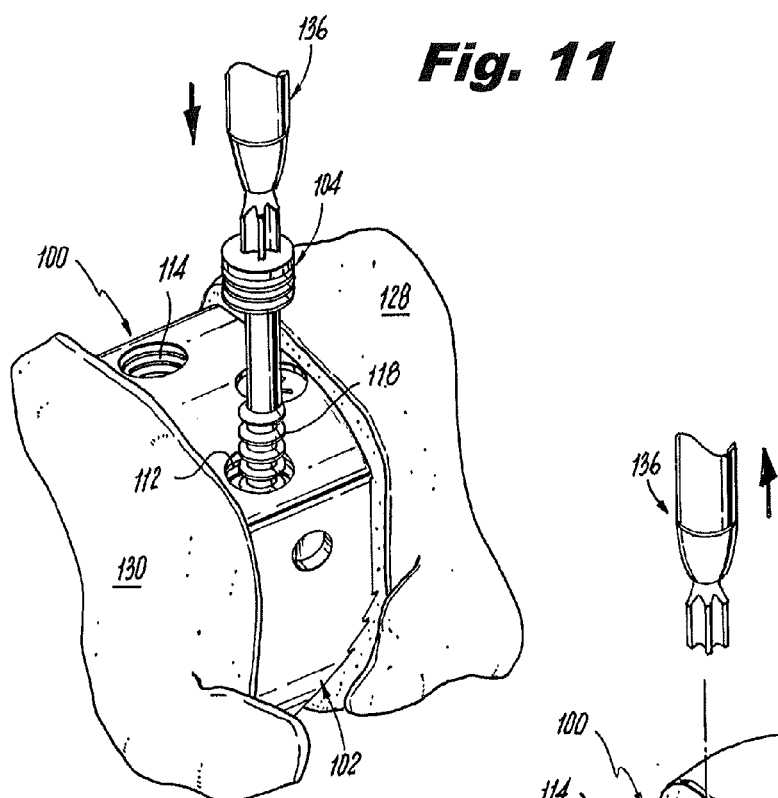
FIG. 11 is a schematic perspective view of the spacer of FIG. 8, showing the first lateral screw being driven into the first lateral bore of the spacer.

With reference now to FIG. 8, with spacer 102 in place, screw 104 is driven into bore entrance 108 of medial bore 106 using a driver 136 configured to mate with the driver features of head 116 of screw 104. As driver 136 turns the flexible screw 104 camming surface 122 of bore 106 cams distal tip 118 of screw 104 to bend shaft 120 and impart the exit angle to the distal tip 118. As shown in FIG. 9, when screw 104 is fully driven into place, tip 118 is angled to engage vertebra 130 to affix spacer 102 to the bone. As indicated in FIG. 10, when screw 104 conforms to bore 106, it bends to be aligned along axis C of bore entrance 108 and out through bore exit 110 along axis D. The threads of head 116 engage corresponding threads in bore entrance 108. As indicated in FIG. 11, the second screw 104 is driven into lateral bore 112 in a similar manner as described above.

Figure 12:
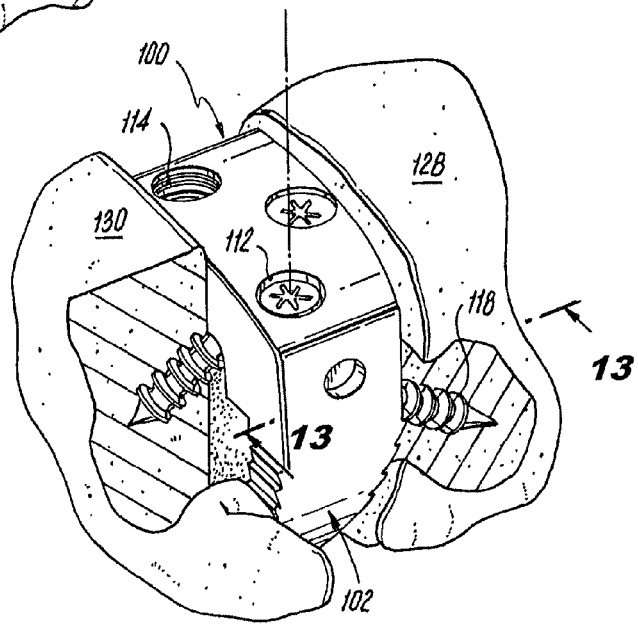
FIG. 12 is a cut away schematic perspective view of the spacer of FIG. 11, showing the first lateral screw affixed to the second vertebra.
Figure 13:
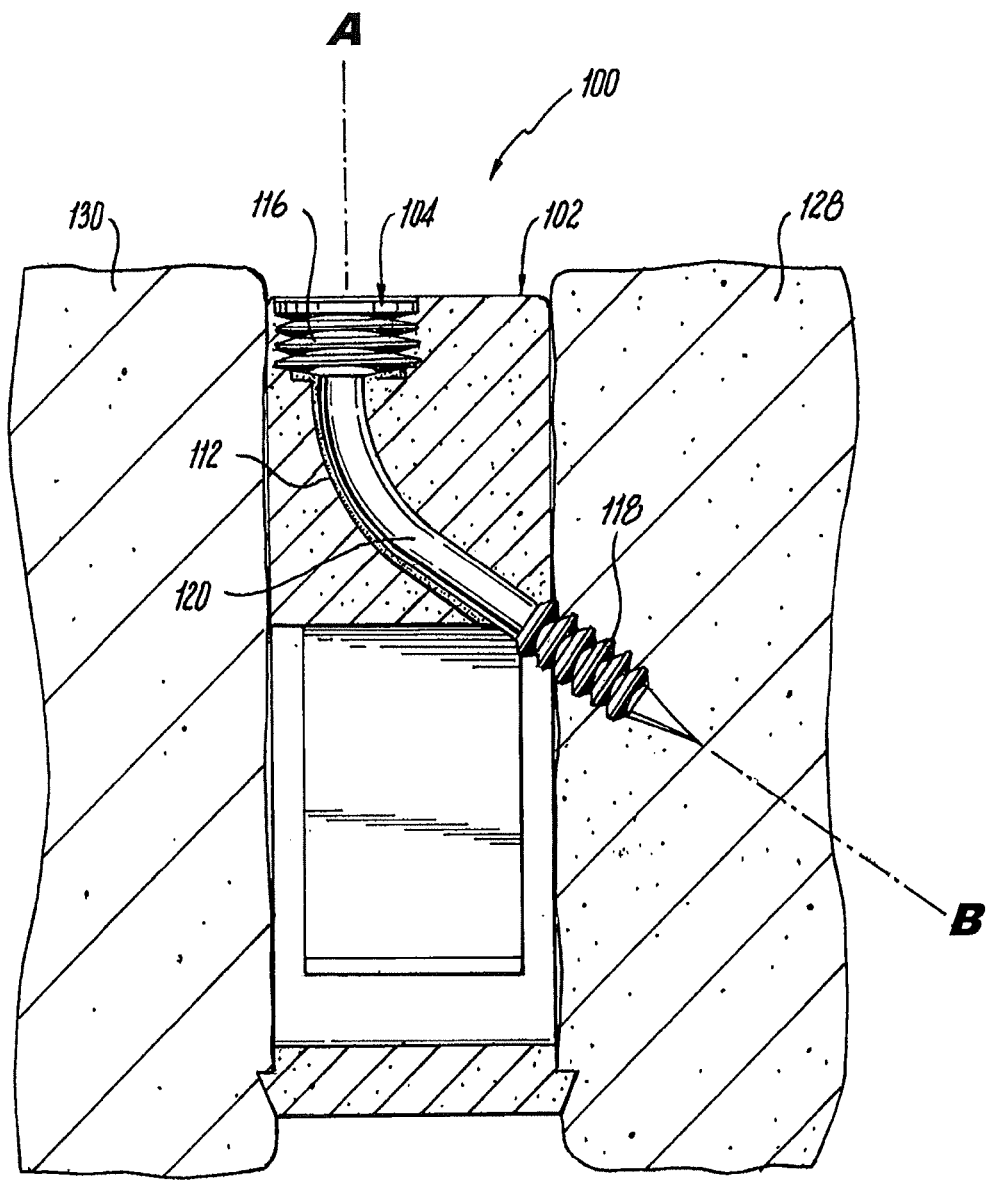
FIG. 13 is a schematic cross-sectional elevation view of the spacer of FIG. 12, showing the first lateral screw in place joining the spacer and the second vertebra together.

As shown in FIGS. 12 and 13, tip 118 of the second screw 104 is driven at the angle of axis B into inferior vertebra 128. This process is repeated for a third screw 104 in bore 114, which results in a the second screw 114 also being affixed to inferior vertebra 128. Since the screws 104 are Herbert screws wherein the thread pitch of tip 118 is different from the thread pitch of head 116, spacer 102 the respective bones are compressed together when the screws 104 are tightened. All three screws 104 are thus driven into spacer 102 at a driver angle substantially perpendicular to an inferior-superior direction defined by the inferior and superior vertebrae. This facilitates implantation because it allows for application of force along the driver axis with significantly reduced risk of tool slippage compared to traditional implants that require the driver to engage the screws at an oblique angle. Those skilled in the art will recognize that the order given above in which the screws 104 are placed is exemplary, and that any suitable order can be used as needed.

Those skilled in the art will readily appreciate that the anterior approach for implanting spacer 102 described above is exemplary, and that the system can readily be implemented from any other suitable approach such as lateral or posterior approaches. The application could be used for anterior lumbar interbody devices (ALIF) as well as with X-LIF and D-LIF approaches from a lateral approach. Furthermore, spacer 102 is shown in a lumbar application, however, spacers such as spacer 102 can be sized for the cervical and thoracic spine. The implant may be made of any biocompatible material, such as for example stainless steel, titanium, titanium alloy, cobalt, cobalt chrome, polyetheretherketone (PEEK) or the like. The implant may be of a unitary, one piece structure or may be made of multiple parts made from the same or different materials. By way of example only, the implant may have a portion made of PEEK and another portion made of titanium. The implant may further include or have added a mechanism for preventing screw back out.

Figure 14:
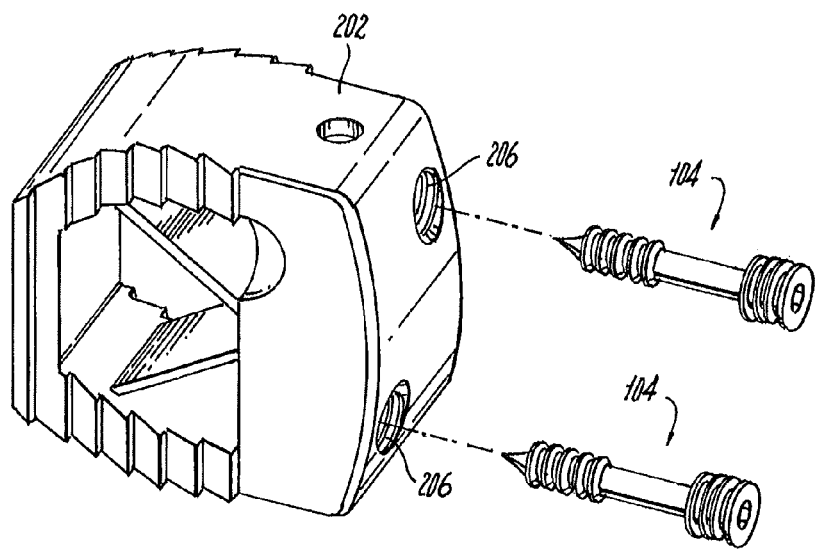
FIG. 14 is a perspective view of another exemplary embodiment of an orthopedic implant system constructed in accordance with the present invention, showing an intervertebral spacer with two flexible Herbert screws.
Figure 15:
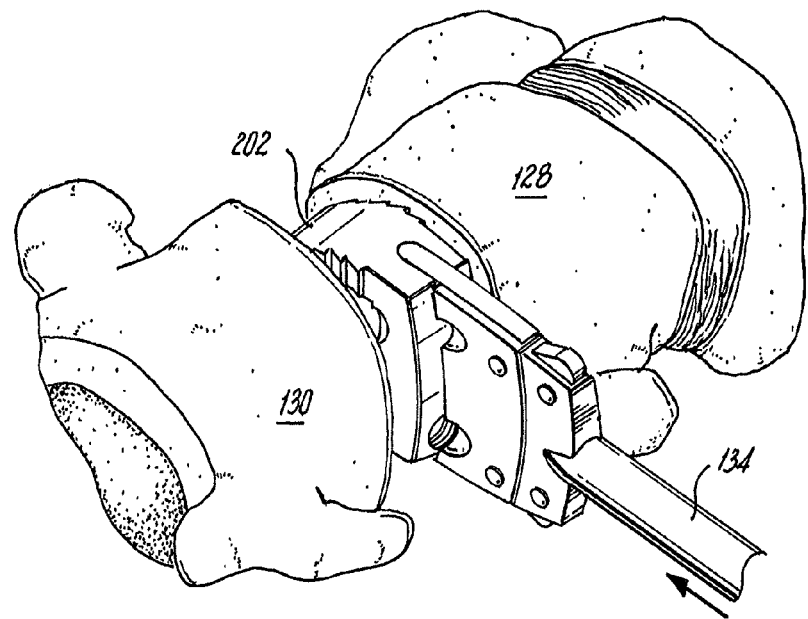
FIG. 15 is a schematic perspective view of the spacer of FIG. 14, showing the spacer positioned in the intervertebral space for implantation from a lateral approach.
Figure 16:
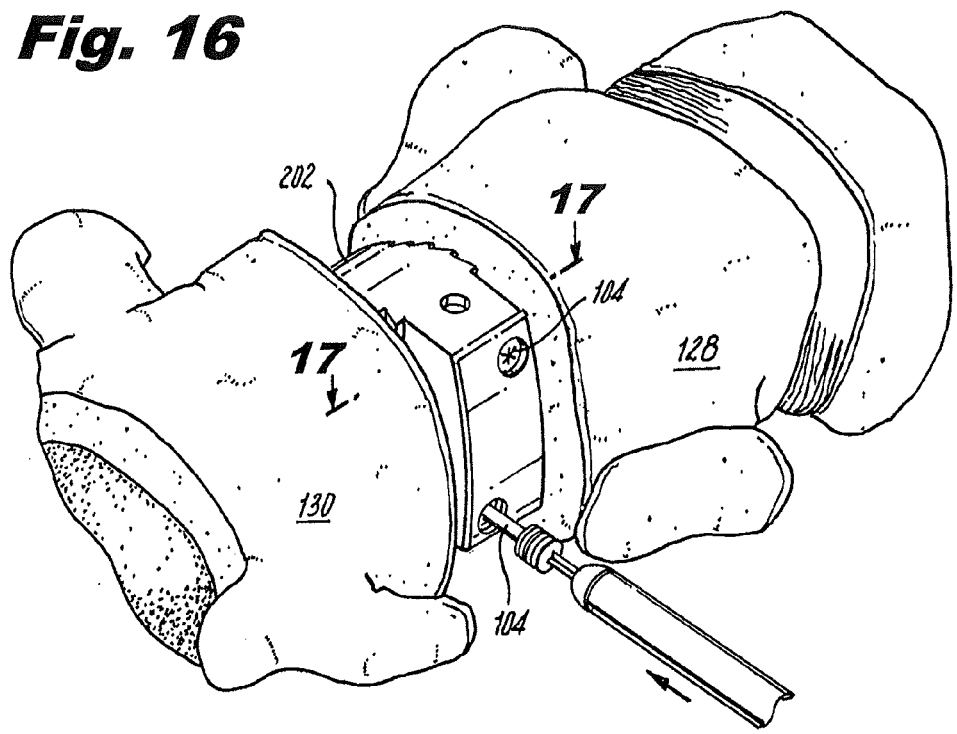
FIG. 16 is a schematic perspective view of the spacer of FIG. 14, showing the second of two screws being driven into the respective bore of the spacer.
Figure 17:
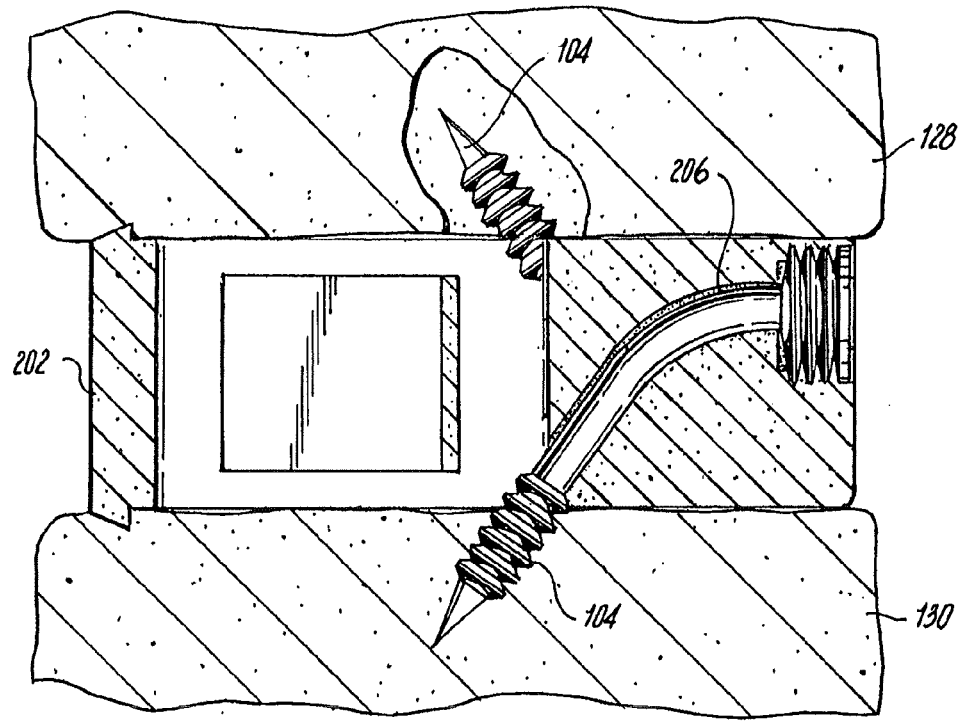
FIG. 17 is a cross-sectional elevation view of the spacer of FIG. 14, showing the two screws in place, one extending from each of two opposite sides of the spacer for joining the spacer and two vertebra together.

Referring now to FIG. 14, another exemplary embodiment of a spacer 202 is shown, similar to spacer 102 described above. The primary difference is that spacer 202 includes two bores 206 instead of three. This allows for a more compact overall size of spacer 202, for example for use in a lateral approach to affix vertebrae 128 and 130 as shown in FIGS. 15. When both screws 104 have been driven into place as indicated in FIG. 16, the curvatures of the respective bores 206 drive one of the screws 104 in a superior direction and one in an inferior direction, as oriented in FIG. 17, so each screw 104 affixes a respective vertebra 128 and 130.

The screw placement through spacers 102 and 202 to the vertebral bodies above and below reduces the need for instrumentation which attaches from the outside of the vertebral margins. Plates and screws or screws attached via rods between vertebral segments have the requirement for greater exposure for application and often are left resting against the visceral or vascular structures with potential long term injury to these structures.

Referring again to FIGS. 1-13, those skilled in the art will readily appreciate that if warranted by a given application, spacer 102 could be inverted so two screws are driven into superior vertebra 130 and one screw is driven into inferior vertebra 128. It is also contemplated that any suitable number of screws and bores can be included without departing from the spirit and scope of the invention. Lateral bores 112 and 114 have parallel exit axes B and F, however it is contemplated that the bores could be modified to have diverging or converging exit axes. Moreover, the exit axis B, D, and F are exemplary in that each forms an angle with its respective entrance axis A, C, and E that is equal to the angles of the other bores, however it is also contemplated that the angle formed by any or all of the bores can be unique from the others without departing from the spirit and scope of the invention.

Figure 18:
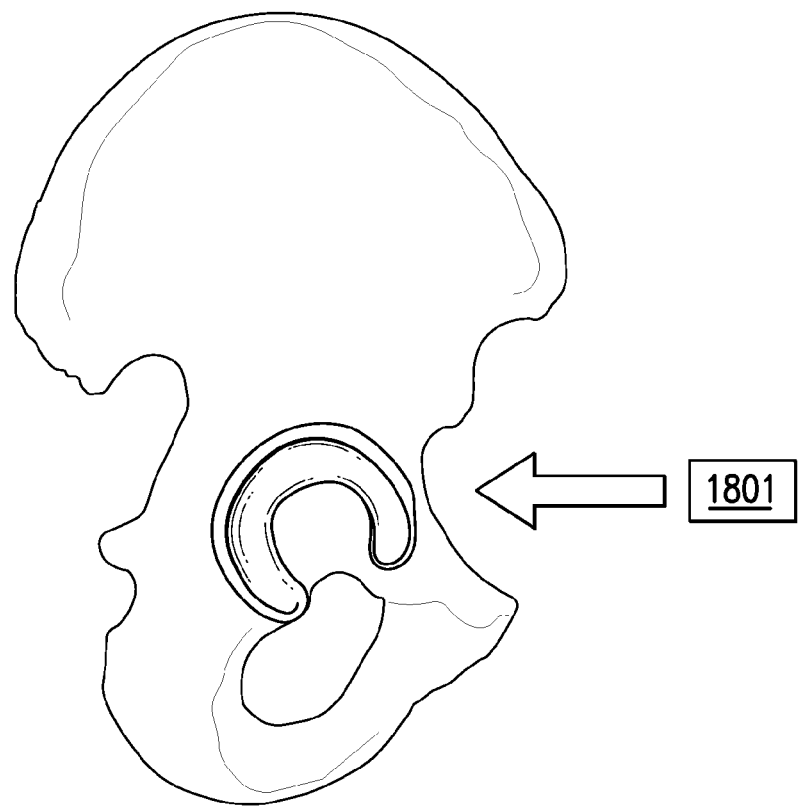
FIG. 18 is a schematic perspective view of a pelvic girdle and an exemplary embodiment of an acetabular cup implant constructed in accordance with the present invention.
Figure 19:
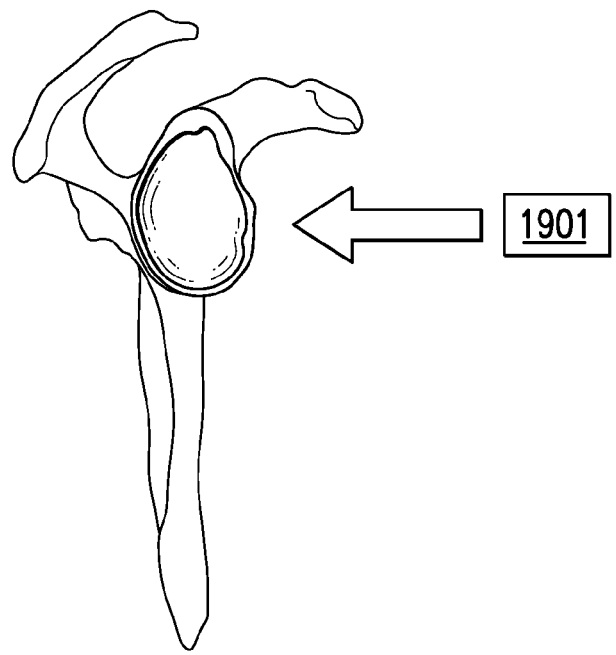
FIG. 19 is a schematic perspective view of a scapula and an exemplary embodiment of a glenoid fossa prosthesis implant constructed in accordance with the present invention.
Figure 20:
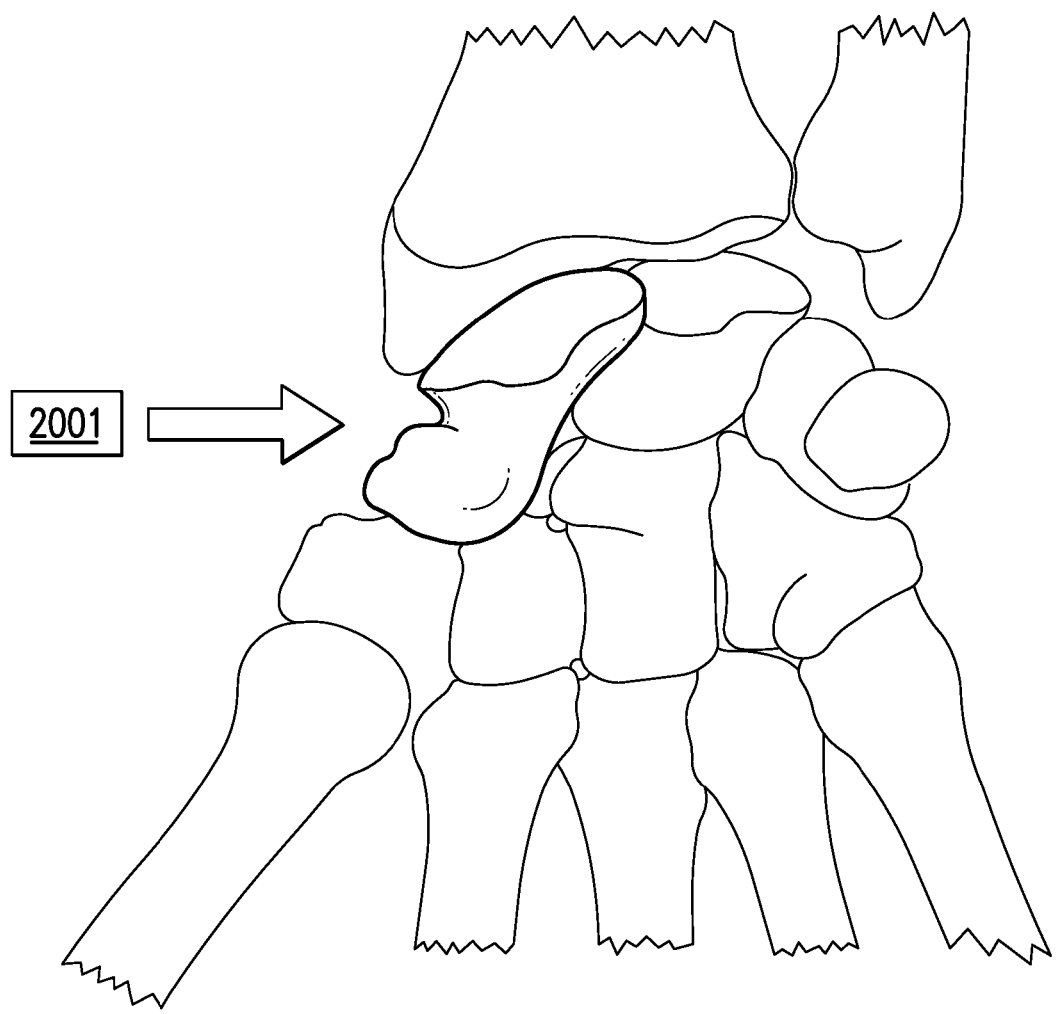
FIG. 20 is a schematic perspective view of wrist bones and an exemplary embodiment of a scaphoid prosthesis implant constructed in accordance with the present invention.

Spacer 102 has been described as an exemplary application of an orthopedic implant in accordance with the subject invention. Those skilled in the art will readily appreciate that any other suitable orthopedic application can attain the advantages described herein without departing from the spirit and scope of the invention. For example, the implant can be an intervertebral spacer. Or, as schematically shown in FIG. 18, the implant can be an acetabular cup 1801. In addition, as schematically shown in FIG. 19, the implant can be a glenoid fossa prosthesis 1901. Or, as schematically shown in FIG. 20, the implant can be a scaphoid prosthesis 2001. The implant can be any other suitable type of implant, and the implant location can be in a cervical spine, thoracic spine, lumbar spine, glenohumoral joint, hip joint, wrist, or in any other suitable location. The systems and methods of the invention reduce the size of the incision required for implantation, allowing for less invasive application of orthopedic implants.

The methods and systems of the present invention, as described above and shown in the drawings, provide for orthopedic implants with superior properties including facilitated implantation, reduced risk of trauma to surrounding tissues, and less invasive procedures. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. An orthopedic implant system comprising:
    an implant configured and adapted for implantation in orthopedic applications, wherein the implant defines a bore therethrough having a cylindrical bore entrance defined along a first axis and a bore exit defining a second axis that is angled with respect to the first axis to facilitate implantation of the implant, wherein at least a portion of the bore entrance includes cylindrical threads; and
    a flexible screw mounted in the bore of the implant, wherein the screw includes a head at one end configured to receive a driver tool for turning the screw within the implant, and a screw tip at an opposite end from the head configured for engaging bone, wherein the tip includes threads, wherein an outer diameter of the threads of the tip is smaller than an inner diameter of the threads of the bore entrance defining a cylindrical clearance therebetween such that the threads of the tip are configured to pass through the bore without engaging the threads of the bore entrance, and wherein a portion of the screw between the tip and the head is flexible to allow bending of the screw passing into the bore of the implant along the first axis and out of the bore of the implant along the second axis.

2. An orthopedic implant system as recited in claim 1, wherein the implant includes a camming surface in the bore for turning the tip of the flexible screw from the first axis to the second axis as the flexible screw is advanced within the bore.

3. An orthopedic implant system as recited in claim 1, wherein the implant is an intervertebral spacer that includes opposed superior and inferior surfaces configured and adapted for engaging the spacer between a superior vertebra and an inferior vertebra, respectively.

4. An orthopedic implant system as recited in claim 3, wherein the first axis and bore entrance are substantially parallel to the superior and inferior surfaces of the spacer, and wherein the bore exit and second axis are angled with respect to the first axis at an angle in the range of about 30° to about 45°.

5. An orthopedic implant system as recited in claim 3, wherein the bore is a first bore and the spacer includes a second bore therethrough having a bore entrance defined along a third axis parallel to the first axis and a bore exit defining a fourth axis that is angled with respect to the third axis, wherein the bore exit of the first bore opens on the superior surface of the spacer, and wherein the bore exit of the second bore opens on the inferior surface of the spacer.

6. An orthopedic implant system as recited in claim 5, wherein the spacer includes a third bore therethrough having a bore entrance defined along a fifth axis parallel to the first axis and a bore exit defining a sixth axis that is angled with respect to the fifth axis, wherein the bore exit of the third bore opens on the inferior surface of the spacer.

7. An orthopedic implant system as recited in claim 1, wherein the bore entrance has a larger diameter than the bore exit.

8. An orthopedic implant comprising an implant body configured and adapted for implantation in orthopedic applications, wherein the implant body defines a bore therethrough having a cylindrical bore entrance defined along a first axis and a bore exit defining a second axis that is angled with respect to the first axis to facilitate implantation of the implant body, wherein at least a portion of the bore entrance includes cylindrical threads, wherein the threads of the bore entrance are configured to allow an outer diameter of threads of a flexible screw tip pass through the bore without engaging the threads of the bore entrance.

9. An orthopedic implant as recited in claim 8, wherein the implant body includes a camming surface in the bore for turning a tip of a flexible screw from the first axis to the second axis as the flexible screw is advanced within the bore.

10. An orthopedic implant as recited in claim 8, wherein the implant body is an intervertebral spacer that includes opposed superior and inferior surfaces configured and adapted for engaging the spacer between a superior vertebra and an inferior vertebra, respectively.

11. An orthopedic implant as recited in claim 10, wherein the first axis and bore entrance are substantially parallel to the superior and inferior surfaces of the spacer, and wherein the bore exit and second axis are angled with respect to the first axis at an angle in the range of about 30° to about 45°.

12. An orthopedic implant as recited in claim 10, wherein the bore is a first bore and the spacer includes a second bore therethrough having a bore entrance defined along a third axis parallel to the first axis and a bore exit defining a fourth axis that is angled with respect to the third axis, wherein the bore exit of the first bore opens on the superior surface of the spacer, and wherein the bore exit of the second bore opens on the inferior surface of the spacer.

13. An orthopedic implant as recited in claim 12, wherein the spacer includes a third bore therethrough having a bore entrance defined along a fifth axis parallel to the first axis and a bore exit defining a sixth axis that is angled with respect to the fifth axis, wherein the bore exit of the third bore opens on the inferior surface of the spacer.

14. An orthopedic implant as recited in claim 8, wherein the implant body is of a type selected from the group consisting of an acetabular cup, a glenoid fossa prosthesis, and a scaphoid prosthesis.

15. A method of implanting an orthopedic implant comprising:
  inserting an implant into an orthopedic implant location, wherein the implant defines a bore therethrough having a cylindrical bore entrance defined along a first axis and a bore exit defining a second axis that is angled with respect to the first axis to facilitate implantation of the implant, wherein at least a portion of the bore entrance includes cylindrical threads; and
  affixing the implant to a bone by driving a flexible screw in through the bore entrance along the first axis and out through the bore exit along the second axis and into the bone, wherein an outer diameter of threads on a tip of the screw is smaller than an inner diameter of the threads of the bore entrance defining a cylindrical clearance therebetween such that the threads of the tip are configured to pass through the bore without engaging the threads of the bore entrance.

16. A method of implanting an orthopedic implant as recited in claim 15, wherein inserting an implant includes inserting the implant into an orthopedic implant location between an inferior vertebra and a superior vertebra and wherein driving a flexible screw includes driving the flexible screw through the bore entrance along the first axis with the first axis substantially perpendicular to an inferior-superior direction defined by the inferior and superior vertebrae.

17. A method of implanting an orthopedic implant as recited in claim 15, wherein inserting an implant includes inserting the implant into an orthopedic implant location selected from the group consisting of the cervical spine, the thoracic spine, the lumbar spine, a glenohumoral joint, a hip joint, and a wrist.

18. A method of implanting an orthopedic implant as recited in claim 15, wherein inserting an implant includes inserting the implant between two vertebrae from an approach selected from the group consisting of an anterior approach, a lateral approach, an x-lif approach and a posterior approach.

19. A method of implanting an orthopedic implant as recited in claim 15, wherein affixing the implant to a bone by driving a flexible screw includes compressing the implant and the bone together with a flexible screw that has a first screw pitch at a proximal end of the screw and a second screw pitch at a distal end of the screw for compressing the bone and implant together.

20. A method of implanting an orthopedic implant as recited in claim 15, wherein driving a flexible screw includes turning the flexible screw with a driver tool engaged to a proximal end of the screw while camming a distal tip of the screw in the bore of the implant to bend the flexible screw and impart an angle of about 30° to about 45° on the distal tip of the screw with respect to the first axis.

21. A method of implanting an orthopedic implant as recited in claim 15, wherein the bone is a first bone, and wherein affixing the implant includes affixing the implant to a second bone by driving a second flexible screw in through an entrance of a second bore in the implant along a third axis parallel with the first axis and out through a respective bore exit along a fourth axis angled relative to the third axis and into a second bone.

\* \* \* \* \*